United States Patent
Jiang et al.

(10) Patent No.: US 7,104,965 B1
(45) Date of Patent: Sep. 12, 2006

(54) INTERACTIVE SYSTEM AND METHOD FOR PERIPHERAL NERVE MAPPING AND BLOCKING

(75) Inventors: Yandong Jiang, North Reading, MA (US); Neelakant Sunder, Winchester, MA (US); Edward George, Waltham, MA (US)

(73) Assignee: The General Hospital Corporation, Boston, MA (US)

( * ) Notice: Subject to any disclaimer, the term of this patent is extended or adjusted under 35 U.S.C. 154(b) by 493 days.

(21) Appl. No.: 10/456,823

(22) Filed: Jun. 6, 2003

(51) Int. Cl.
- *A61B 5/05* (2006.01)
- *A61N 1/00* (2006.01)
- *A61N 1/04* (2006.01)
- *A61N 1/05* (2006.01)
- *A61N 1/06* (2006.01)

(52) U.S. Cl. ...................... 600/554; 607/116

(58) Field of Classification Search ............... 600/554, 600/386, 390, 393, 372; 606/32, 33–41; 607/115, 116
See application file for complete search history.

(56) References Cited

U.S. PATENT DOCUMENTS

| | | | |
|---|---|---|---|
| 4,934,377 A * | 6/1990 | Bova et al. .................. | 600/509 |
| 4,938,223 A | 7/1990 | Charters et al. | |
| 4,950,233 A | 8/1990 | Abramowitz | |
| 5,284,153 A | 2/1994 | Raymond et al. | |
| 5,333,618 A * | 8/1994 | Lekhtman et al. .......... | 600/547 |
| 5,560,372 A * | 10/1996 | Cory ........................... | 600/554 |
| 5,618,274 A | 4/1997 | Rosenthal | |
| 5,853,373 A | 12/1998 | Griffith et al. | |
| 6,058,938 A * | 5/2000 | Chu et al. .................... | 128/898 |
| 6,122,544 A * | 9/2000 | Organ ........................ | 600/547 |
| 6,298,256 B1 | 10/2001 | Meyer | |
| 6,325,764 B1 | 12/2001 | Griffith et al. | |
| 6,391,005 B1 | 5/2002 | Lum et al. | |
| 6,466,817 B1 | 10/2002 | Kaula et al. | |
| 6,478,769 B1 | 11/2002 | Parker | |
| 6,500,128 B1 | 12/2002 | Marino | |
| 6,533,732 B1 * | 3/2003 | Urmey ........................ | 600/554 |
| 6,535,759 B1 * | 3/2003 | Epstein et al. .............. | 600/547 |
| 6,564,078 B1 * | 5/2003 | Marino et al. .............. | 600/373 |
| 6,837,884 B1 * | 1/2005 | Woloszko .................... | 606/32 |
| 6,904,324 B1 * | 6/2005 | Bishay ........................ | 607/149 |

FOREIGN PATENT DOCUMENTS

| | | |
|---|---|---|
| EP | 0 637 934 B1 | 7/2000 |
| WO | WO 93/20751 A1 | 10/1993 |

(Continued)

*Primary Examiner*—Max F. Hindenburg
*Assistant Examiner*—Matthew Dryden
(74) *Attorney, Agent, or Firm*—Daly, Crowley, Mofford & Durkee, LLP

(57) ABSTRACT

A system for providing nerve mapping in human patients, which includes a processor coupled to a pulse generator and to a multi-position switch. The system further includes a conductive needle having a first end adapted for insertion into tissue and a second end coupled to a negative terminal of the pulse generator. A plurality of electrodes are disposed on the skin of the patient in a ring arrangement for defining a bounded area. Each electrode is selectively coupled to a positive terminal of the pulse generator, via the multi-position switch. In this arrangement, at least one pulse can be applied to the first end of the conductive needle while the conductive needle is positioned in the bounded area to form a communication relationship between the first end of the conductive needle and at least one of the plurality of electrodes for exciting a nerve located in the bounded area.

25 Claims, 5 Drawing Sheets

FOREIGN PATENT DOCUMENTS

WO   WO 01/93748 A3   12/2001

WO   WO 02/09584 A1   2/2002

* cited by examiner

INTERACTIVE SYSTEM AND METHOD FOR PERIPHERAL NERVE MAPPING AND BLOCKING

FIELD OF THE INVENTION

The present invention relates generally to a system for nerve mapping, and more particularly to a method and apparatus for identifying a proximate nerve location for administration of a nerve blocking agent or solution.

BACKGROUND

As is known in the art, a nerve block is achieved by delivering a local anesthetic solution proximate to a nerve to be blocked. Typically, the anesthetic solution is delivered by inserting a needle such that the anesthetic solution can be injected in close proximity to the nerve to be blocked. To correctly position the needle, it is necessary to identify the nerve location prior to the injection of the local anesthetic solution.

One conventional technique used to correctly position the needle proximate to a nerve is to elicit paresthesic. This technique, however, is not a reliable way to position the needle proximate to the nerve because of individual traits of each patient, such as patient nervousness, patient sedation, patient communication skills and/or cooperation. In addition, some patients may not sense paresthesia, and thus, if the needle is inserted into a motor nerve bundle, nerve damage may occur due to the tip of the needle being too close to the motor nerve or motor nerve bundle or the needle being inserted directly into the nerve, while injecting the local anesthetic solution. The elicitation of paresthesia technique, as described above, is also very time consuming.

In attempts to provide alternatives to the above-described elicitation of paresthesia technique, mechanical aids including radioscopy and a peripheral nerve stimulation (PNS) technique have been introduced into practice. The radioscopy technique includes using the X-ray to find the bones as landmarks and to position the needle under X-ray assuming the operator knows the spatial relation between the bone landmark and the nerve to be blocked. There are several drawbacks for this technique including: it requires X-ray equipment; the patient has to be exposed to X-ray; the operator needs to be trained to use X-ray equipment; the end of the point of approximation of the needle to the nerve is not defined prior to delivery of local anesthetics; and it is also time consuming.

The PNS technique uses the basic principle that a rectangular electrical pulse having a predetermined threshold of direct current and duration can depolarize a nerve cell membrane. In practice, the PNS technique uses an insulated needle as a negative electrode, which is inserted into human tissue in a region to receive a nerve blocking solution. The PNS technique further uses a positive electrode, which is placed somewhere on the patients skin as a current return path. An electrical pulse is emitted from the tip of the needle and travels through the tissue to the positive electrode. If the nerve to be blocked is located in between these two electrodes and the current density (current per unit of cross-section area) and the pulse width are at or above the predetermined threshold, the electrical pulse causes depolarization of the nerve axon, which causes contraction (or a twitch) of the muscle being innervated by the motor nerve. The current required to depolarize the nerve and trigger the corresponding muscle contraction is related to the distance between the tip of the needle and the nerve. This information is used as a guide for positioning the tip of the needle to a location proximate to the nerve to be blocked prior to delivering the local anesthetic. The lower the current required, the closer the tip of the needle to the nerve.

One drawback of the PNS technique is that it uses only one positive electrode, which restricts an operator (e.g., clinician) to obtaining only two-dimensional position information for positioning the tip of the needle close to the nerve. This drawback is further exacerbated in that it is not clear where the positive electrode should be located on the patient's skin for providing the electrical current return path for the pulse emitted from the tip of the needle.

Therefore, an unsolved need remains for a system for providing nerve mapping that overcomes the above-described limitations and drawbacks of the prior art.

SUMMARY OF THE INVENTION

A system for providing nerve mapping is set forth in accordance with one aspect of the present invention. The system includes a processor coupled to a control input of a pulse generator and to a control input of a multi-position switch. The processor is further coupled to an image display and to a database. The system further includes a conductive needle having a first end adapted for insertion into tissue and a second end coupled to a first terminal of the pulse generator. A second terminal of the pulse generator is coupled to an input of the multi-position switch. A plurality of output terminals of the multi-position switch are coupled to an equal plurality of electrodes. The plurality of electrodes are disposed on the skin of a human patient in a ring arrangement, which defines a bounded area. The plane of the ring is perpendicular to the longitudual axis of the nerve and at the level of which the nerve to be blocked.

The control input of the multi-position switch is adapted to receive a plurality of control signals from the processor for selectively coupling the second terminal of the pulse generator to one of the plurality of electrodes. Further, the control input of the pulse generator is adapted to receive a plurality of control signals from the processor for controlling the pulse generator to provide at least one pulse to the first end of the conductive needle, while the conductive needle is positioned in the bounded area. In this arrangement, one or more pulses emitted from the first end of the conductive needle are received by each one of the plurality of electrodes in sequence. By observing the response (muscle twitch) generated by an electrical pulse between the conductive needle and each of the plurality of electrodes, it is possible to locate the nerve in the bounded area.

In one aspect of the invention, the image display is adapted to provide at least one image depicting a proximity of the first end of the needle to the nerve. The display can also display a plurality of model muscle contractions, which is the one the operator is looking for and can be selected from a library of model muscle contractions stored in the database.

In one aspect of the invention, a non-conductive medium, such as polyimide, is employed to retain each of the plurality of electrodes in the ring arrangement and having a predetermined spacing relative to each other for defining the bounded area.

In one aspect of the invention, the conductive needle includes a control for adjusting an energy level of the at least one pulse, which is provided to the conductive needle from the pulse generator, to permit a minimal energy value to be applied to the first end of the needle to excite the nerve. In one example, the at least one pulse is provided having a pulse width in the range of about 1 milli-seconds (ms) to about 0.5 ms and a current in the range of about zero milli-amperes (mA) to about 2 mA.

In one aspect of the inventions, the multi-position switch includes a solid-state switch. In another aspect, the multi-position switch includes a multiplexor.

In accordance with a further aspect of the present invention, a method for providing nerve mapping includes positioning the conductive needle at a predetermined location in a region of tissue bounded by a plurality of electrodes and applying at least one pulse to a first end of a conductive needle to excite a predetermined nerve located in the region of the tissue bounded by the plurality of electrodes. The method further includes measuring at least one actual muscle contraction, which occurs between the first end of the needle and the at least one electrode of the plurality of electrodes, in response to excitation of the predetermined nerve.

Prior to applying the at least one pulse, the method further includes determining a proximate nerve blocking location for which the predetermined nerve is to be blocked. The plurality of electrodes are disposed on the proximate nerve blocking location of the tissue in a ring arrangement, which forms the region of the tissue bounded by the plurality of electrodes.

In addition, a proximate depth "d" is defined for which a nerve is to be blocked. Thereafter, the conductive needle is positioned proximate to the nerve blocking location and at the first end of the conductive needle is inserted to the proximate depth "d."

In an aspect, measuring the at least one actual muscle contraction includes comparing the at least one actual muscle contraction to a model muscle contraction displayed on a display. The method further includes determining if the at least one actual muscle contraction substantially matches the model muscle contraction displayed on the display.

If it is determined that the at least one actual muscle contraction substantially matches the model muscle contraction displayed on the display, the method further includes determining a relative spatial relationship between the first end of the conductive needle and the predetermined nerve, as well as determining a distance value between the first end of the conductive needle and the predetermined nerve. The relative spatial relationship and the distance value are processed to generate a needle position image, which shows a relative proximity of the first end of the conductive needle to the predetermined nerve. Thereafter, an operator viewing the needle position image can move the first end of the needle under interactive guidance of the needle position image to a nerve blocking position for administration of a nerve blocking agent.

If it is determined that the at least one actual muscle contraction does not match the model muscle contraction displayed on the display, the operator can move the tip of the needle to another predetermined position in the region of tissue bounded by the plurality of electrodes and repeat the above-described process.

In accordance with a further aspect of the present invention, a method for nerve mapping includes arranging a plurality of electrodes to form a bounded region on a surface, positioning a conductive needle within the bounded region, providing a first conductive path between the conductive needle and a first one of the plurality of electrodes, applying at least one electrical pulse to the bounded region through the conductive needle, and measuring a nerve response through the first conductive path. The method further includes providing a second conductive path between the conductive needle and a second one of the plurality of electrodes, applying at least one electrical pulse to the bounded region through the conductive needle and measuring a nerve response through the second conductive path.

BRIEF DESCRIPTION OF THE DRAWING

The foregoing and other objects of this invention, the various features thereof, as well as the invention itself, can be more fully understood from the following description, when read together with the accompanying drawings in which.

DETAILED DESCRIPTION OF THE INVENTION

A system for providing peripheral nerve mapping in human body is set forth in accordance with principles of the present invention. The system can be employed by a number of medical personnel, such as doctors, and/or medical technicians, to provide information related to a nerve to be blocked including, but not limited to, a visual indication of a nerve to be blocked and a relative distance between a conductive needle, which is used to administer a nerve blocking agent, and the nerve to be blocked.

Figure 1:
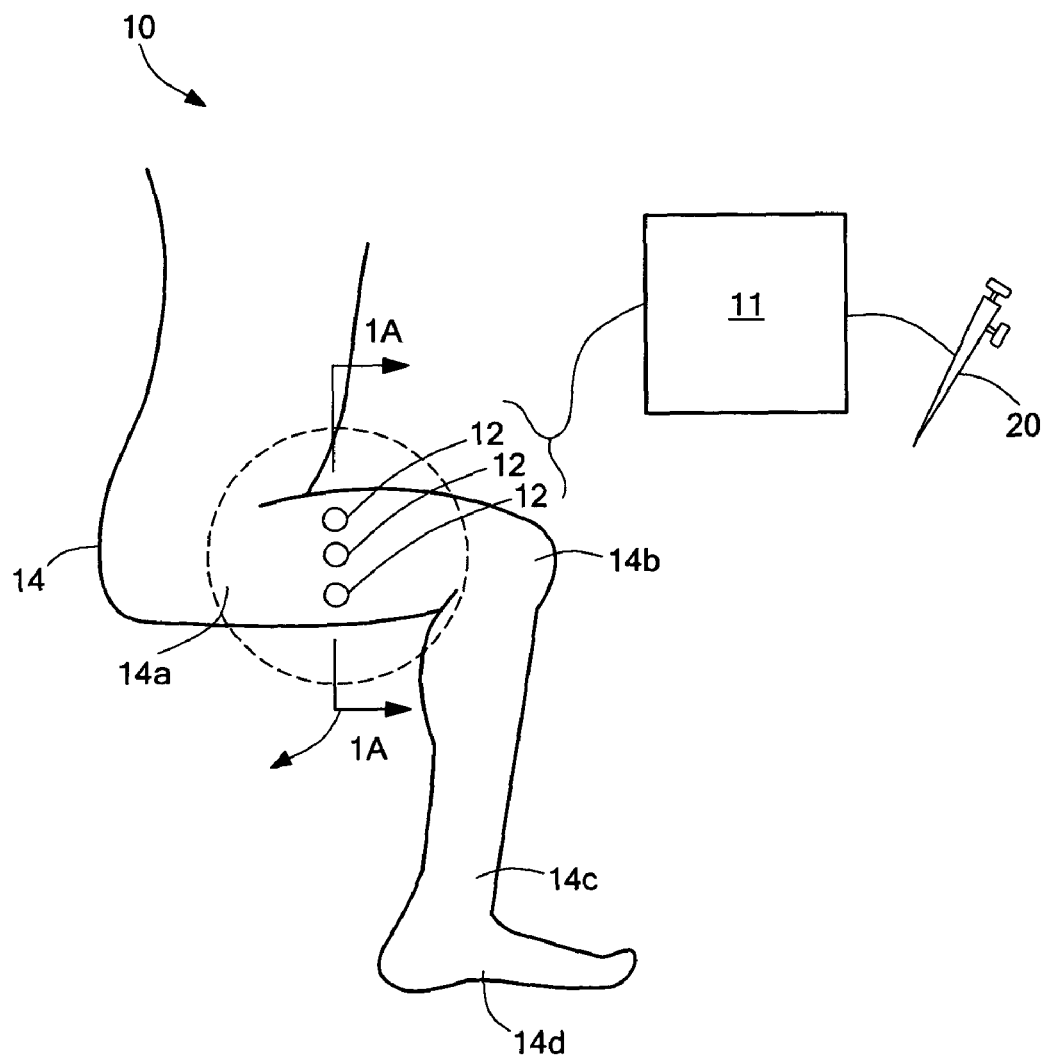
FIG. 1 is a nerve mapping system in accordance with the present invention.

Referring now to FIG. 1, one exemplary embodiment of a system 10 for providing peripheral nerve mapping in human body in accordance with the principles of the present invention is shown. The system includes a plurality of electrodes (generally denoted 12 in FIG. 1). Uniformly disposed on skin 14. The electrodes 12 are disposed in a ring arrangement so as to encircle an area of the human body 14 (e.g. a thigh). The electrodes are couples to a nerve mapping electronics portion 11. The nerve mapping electronics portion 11 and operation of the nerve mapping system will be described in detail below.

Figure 1A:
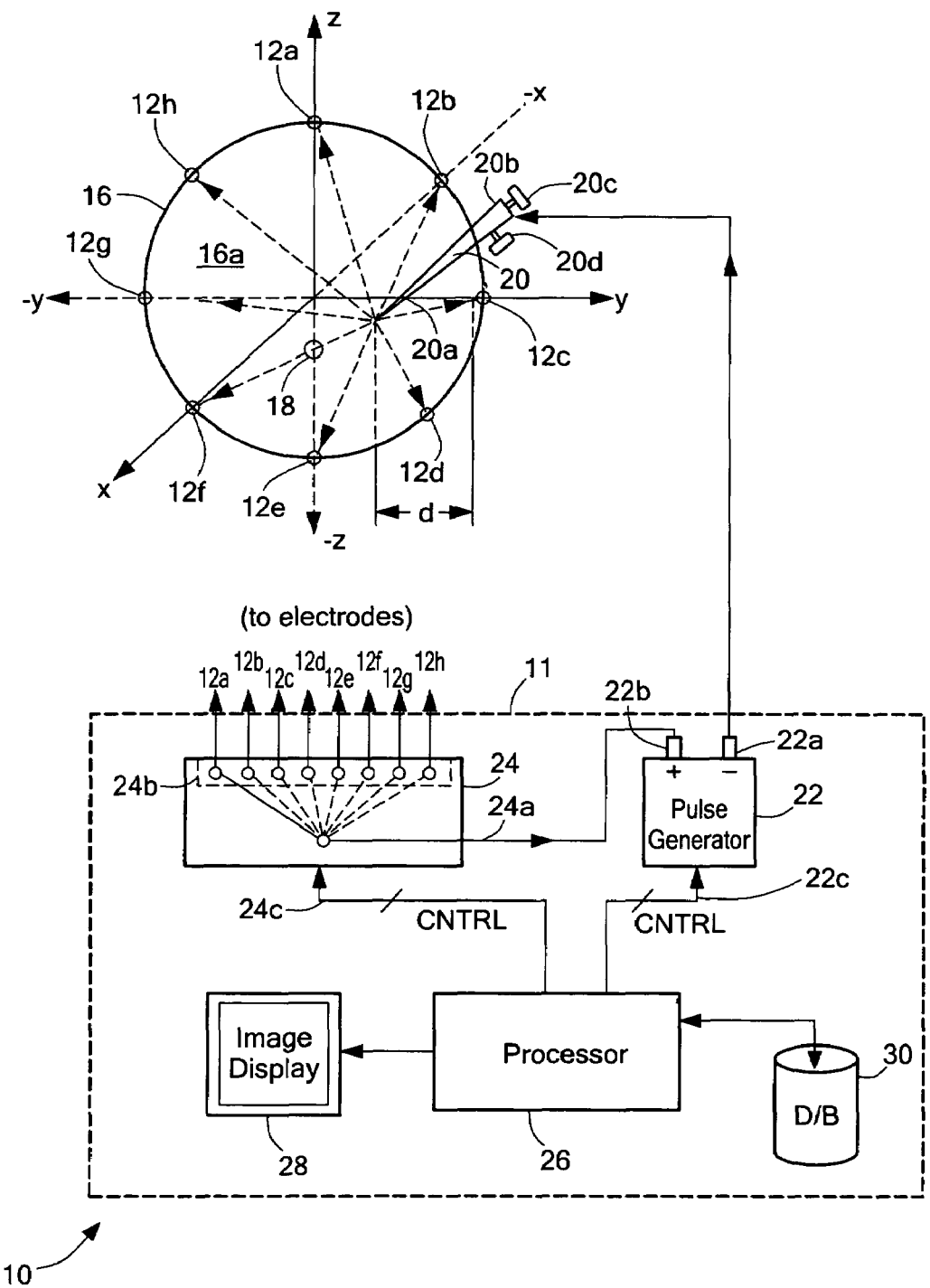
FIG. 1A is a an expanded view of the nerve mapping system of FIG. 1.

Referring now to FIG. 1A in which like elements of FIG. 1 are provided having like reference designations. The system 10 includes the plurality of electrodes 12, which collectively represents electrodes 12a–12h, uniformly disposed on the skin 14 (FIG. 1) in a ring arrangement for encircling the area of the body 14 and forming a bounded area 16. The bounded area 16 includes a nerve blocking plane 16a that corresponds to a plane defined by the cross-sectional arrows 1A—1A in FIG. 1, which are taken at a level or location at which a sample nerve 18 is to be blocked (e.g. thigh region). In the exemplary embodiment, the sample nerve to be blocked lies approximately on the negative z-axis of the nerve blocking plane 16a.

The system 10 further includes a conductive needle 20, which has a first end 20a adapted for insertion into the body part 14 by an operator of the system 10 and a second end 20b that is coupled to a first terminal 22a of a pulse generator 22 located on the nerve mapping electronics portion 11. A second terminal 22b of the pulse generator 22 is coupled to an input terminal 24a of a multi-position switch 24, which is also included on the nerve mapping electronics portion 11. In the exemplary embodiment, the first terminal 22a corresponds to a negatively polarized terminal of the pulse generator 22, while the second terminal 22b corresponds to a positively polarized terminal of the pulse generator 22. Further, a plurality of output terminals 24b of the multi-position switch 24 are coupled to corresponding ones of the plurality of electrodes 12. The nerve mapping electronics portion 11 of the system 10 further includes a processor 26, which is coupled to a control input 24c located on the multi-position switch 24 for providing a plurality of control signals to the multi-position switch 24 to actuate the multi-position switch to selectively couple the second terminal 22b of the pulse generator 22 to one of the plurality of electrodes 12, via the input 24a and one of the outputs 24b of the multi-position switch 24. The processor 26 is also coupled to a control input 22c located on the pulse generator 22 for providing control signals to the pulse generator 22, which operate to control various characteristics of signals provided at the first terminal 22a of the pulse generator 22 (e.g., pulse shape, amplitude and duration). The processor 26 is further coupled to an image display 28 and to a database or library 30, each of which can be located on the nerve mapping electronics portion 11 or can be remotely located outside of the nerve mapping electronics portion 11.

In the exemplary embodiment, the plurality of electrodes 12 can be similarly constructed and arranged as electrodes employed for an electrocardiogram (ECG/EKG), which are known for sensing electrical signals from a human heart, for example. In one embodiment, the plurality of electrodes 12 can be uniformly retained in position to form the ring, as described above, using an electrically conductive adhesive to securely hold the electrodes 12 on the human skin 14. The plurality of electrodes 12 can be disposed on a planar skin, such as a planar surface of a torso (e.g., chest area or back skin tissue 14) by encircling a portion of a limb. For example, the plurality of electrodes 12 can be securely attached to encircle a human patient's right thigh 14a, as shown in FIG. 1. In this arrangement a first predetermined number of the plurality of electrodes 12 can be uniformly spaced about the periphery of the human patient's right thigh 14a during a nerve mapping and/or blocking process for the patent's right knee 14b, for example.

Figure 2:
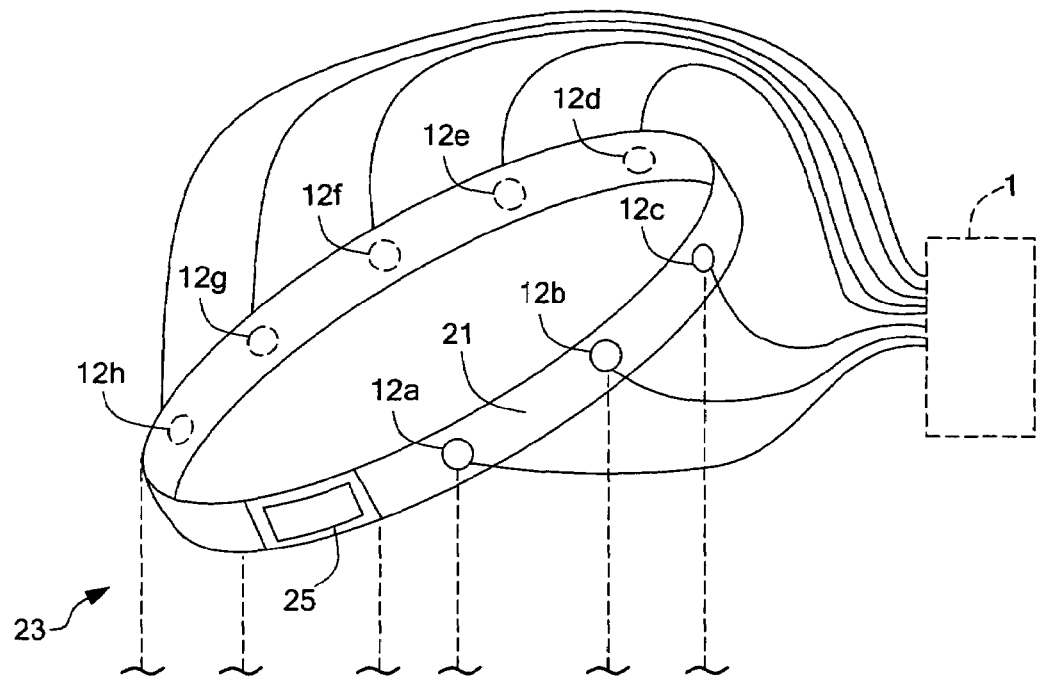
FIGS. 2 and 2A show an embodiment of a flexible structure employed for retaining a plurality of electrodes in a predetermined orientation.
Figure 2A:
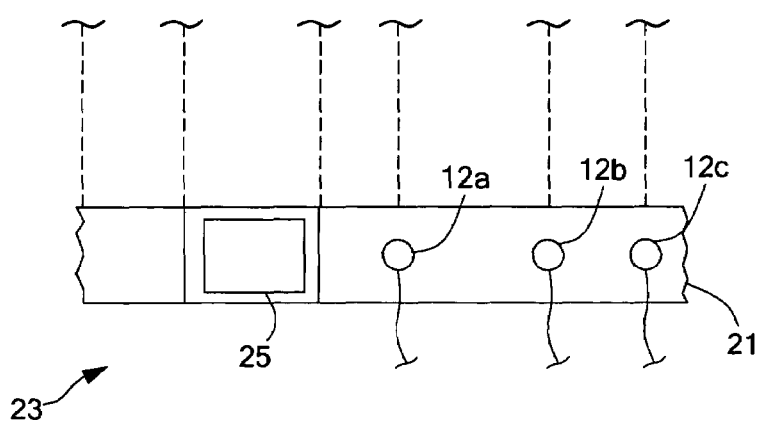

Referring collectively to FIGS. 1, 2A, and 2B, in another embodiment of the present invention, the plurality of electrodes can be uniformly spaced and retained in position on a flexible dielectric material 21, such as polyimide (e.g., Kapton, which is produced by Dupont) to form an adjustable belt-like structure. The dielectric material 21 of the belt-like structure 23 can be bent, formed, and/or molded to provide a ring shape.

The adjustable belt-like structure 23 further includes a coupling mechanism 25, such as a buckle or hook and loop fastener, for securely retaining the belt-like structure 23 in position during use. For example, the belt-like structure 23 including the electrodes 12 can be adjusted using the coupling mechanism 25, to a first position to conformingly and securely encircle a human patient's right thigh 14a. In this arrangement, a first predetermined number of electrodes 12 can be uniformly spaced about the periphery of the human patient's right thigh 14a during a nerve mapping and/or blocking process for the patent's right knee 14b.

In another example, the belt-like structure 23 including the electrodes 12 can be re-adjusted using the coupling mechanism 25 to a second position to conformingly and securely encircle a human patient's right ankle 14c during a nerve mapping and blocking process for the patent's right foot 14d. In this arrangement, a second predetermined number of electrodes, can be uniformly spaced about the periphery of the human patient's right ankle 14c. It should be understood that the first predetermined number of electrodes secured the patients right thigh 14a includes a greater number of electrodes than the second predetermined number of electrodes secured to the patients right ankle 14c because the circumference of the patients thigh 14a is greater than the circumference of the patients ankle 14c.

In the exemplary embodiment, the plurality of electrodes 12 includes eight electrodes uniformly spaced about the thigh in a ring arrangement. Thus, an electrode is positioned approximately every 45 degrees around the thigh 14a. The electrodes 12 thus form and define the bounded area 16 under testing for nerve location identification and/or mapping. It should be understood that additional or fewer than eight electrodes 12 can be employed in the system 10 for providing nerve mapping depending upon the desired nerve location, type and/or desired mapping resolution. Similarly, although in a preferred embodiment, the electrodes 12 are spaced approximately every 45 degrees, in some applications it may be desirable to space the electrodes 12 by more or fewer than 45 degrees. For example, the electrodes may be spaced by 30 or 60 degrees.

In the exemplary embodiment, the conductive needle 20 is provided as a conventional conductive needle that includes an insulated portion, which permits an operator to securely hold the conductive needle 20 without risk of receiving an electrical shock. The conductive needle 20 is further adapted to administer a nerve blocking agent by depressing an injection button 20c after the operator has determined that the first end 20a (e.g. the tip) of the conductive needle 20 is suitably positioned in the human tissue 14 proximate the sample nerve 18 to be blocked. In one embodiment, the conductive needle 20 further includes an adjustable pulse control switch 20d, which can be actuated to adjust attributes of a pulse emitted from the first end 20a of the conductive needle 20, such as an energy value associated with the pulse.

In the exemplary embodiment, the pulse generator 22 can include circuitry for providing a plurality of adjustable output signals at the first terminal 22a, such as square waves, sawtooth waves and/or impulses, which each have controllable amplitudes and durations based on the control signals received from the processor 26 at the control input 22c. The plurality of adjustable output signals, which are provided out of the first terminal 22a of the pulse generator 22, are ultimately delivered to the conductive end portion 20a of the conductive needle 20, as will be described in further detail below. In one embodiment, at least one pulse having an amplitude ranging from approximately 0 Amperes to approximately 2 Amperes and a pulse width (e.g. pulse duration) ranging from approximately 0.1 ms to approximately 0.5 ms is provide at the first end 20a of the conductive needle 20.

The pulse generator 22 further includes a short circuit detection safety feature (not shown), which is adapted to provide an alert to an operator that a patient is grounded elsewhere and to avoid an electrical field from being accidentally directed across a patient's heart, which may cause arrhythmia particularly ventricular tachycardia or ventricular fibrillation. The short circuit detection safety feature provides that electrical current will only flow between the first end 20a of the conductive needle 20 and one of the positive electrodes 12. In an embodiment, the short circuit detection safety feature includes a second transformer, which is shunted across the first 22a and second 22b terminals of the pulse generator 22. The short circuit detection safety feature further includes a first current sensors coupled in series between the first terminal 22a (e.g., negative terminal) and the second transformer and a second current sensor couple in series between the second terminal 22b (e.g., positive terminal) and the second transformer. If both the first and second current sensors sense the same current magnitude, no current leakage exists, and thus the patient is not short circuited elsewhere, as described above. However, if the first and second sensors sense different current magnitudes, a current leakage exists, and thus an operator is notified or alerted to investigate before proceeding with the nerve blocking process.

In the exemplary embodiment, the multi-position switch 24 can include one or more solid state switches capable of rapidly actuating to selectively couple the second electrode 22b of the pulse generator 22 to any one of the plurality of electrodes 12, via the input 24a and one of the plurality of outputs 24b of the multi-position switch 24. It should be understood that the multi-position switch 24 can include a plurality of outputs 24b to accommodate an equal plurality of electrodes 12. In one embodiment, the multi-position switch 24 includes a multiplexor. Those of ordinary skill in the art will appreciate, of course, that any type of switching device can be used including, but not limited to, programmable devices.

In the exemplary embodiment, the processor 26 can include a conventional computer server, such as an "NT-Server," which can be provided by Microsoft of Richmond, Wash., a "Unix Solaris Server," which can be provided by Sun Micro Systems of Palo Alto, Calif. or any one of a number of personal computers, as are known. The processor can be programmed to integrate the information regarding the spatial relation between the first end 20a of the conduction needle and the nerve and display the spatial relation on a computer screen.

In the exemplary embodiment, the image display 28 can include a color cathode-ray tube (CRT), plasma display, or the like, which is adapted to display one or more of a number of model muscle contraction images and/or Nuclear Magnetic Resonance (NMR) images. The model muscle contraction images and/or NMR images are stored in the database 30 library and can be employed to provide a model image of an expected muscle contraction in response to excitation of a predetermined nerve.

Figure 3:
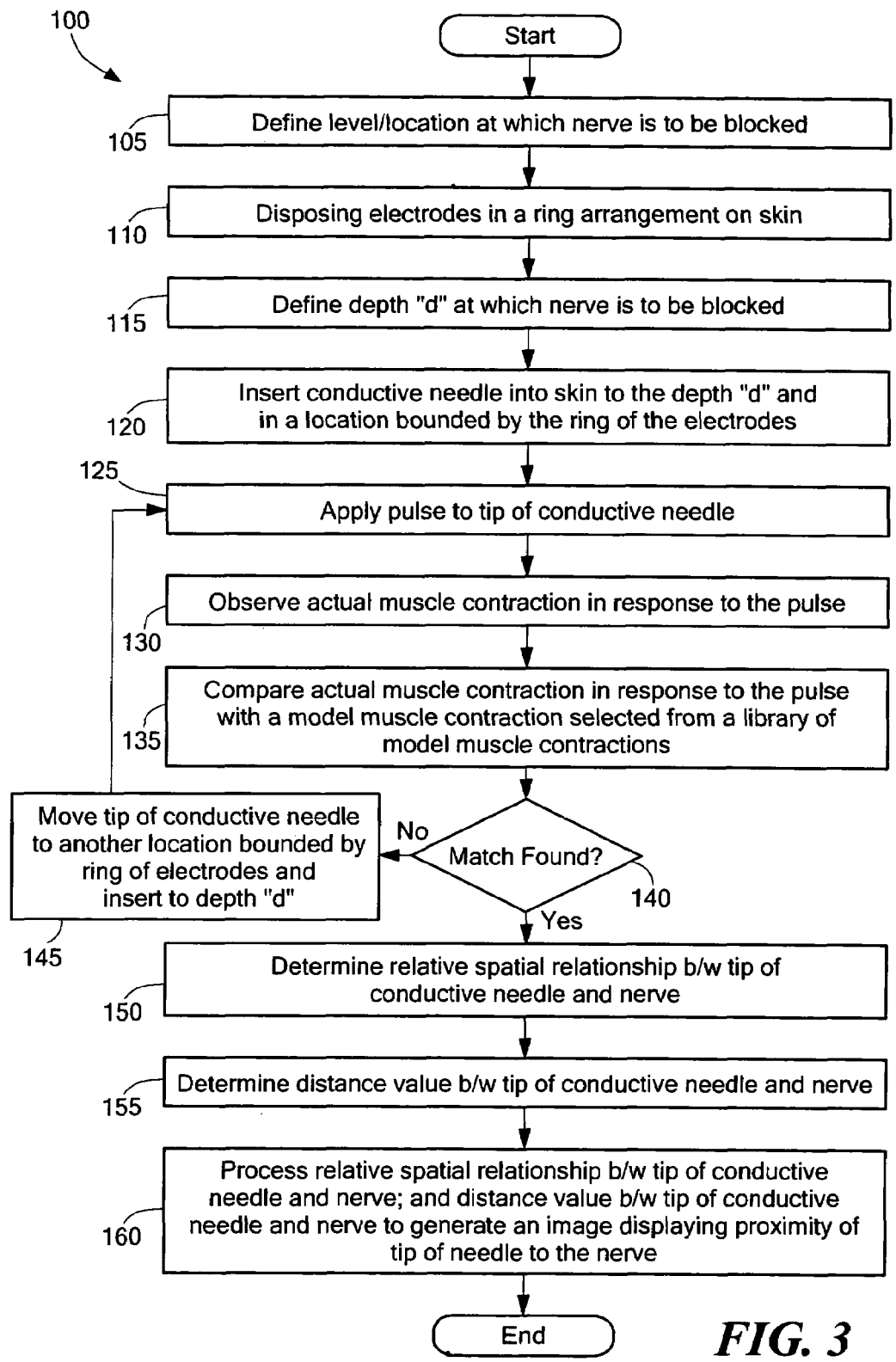
FIG. 3 is a flow chart illustrating a method for nerve mapping.

Referring collectively to FIGS. 1, 1A and 3, FIG. 3 shows a method 100 executable on the system 10 of FIG. 1A for providing nerve mapping in the human body 14. At step 105, the method 100 commences by defining a level and/or location at which a first predetermined nerve is to be blocked. For example, a patient's right knee 14b may need surgery and thus a portion of the popliteal nerve, which is exemplified by the sample nerve 18 and substantially traverses the longitudinal length of the patent's right leg, may require local anesthesia at a point located upstream or above the right knee 14b, such as at a point located within the nerve blocking plane 16a, as described above with respect to FIG. 1A.

At step 110, a plurality of electrodes 12 are disposed on the skin of the patent's right thigh 14a in a ring arrangement along the periphery of the nerve blocking plane 16a. In one embodiment, the plurality of electrodes 12 includes eight electrodes that are positively polarized by virtue of their intermittent coupling to the second terminal 22b (e.g. positive terminal) of the pulse generator 22, via the multi-position switch 24. The plurality of electrodes 12 can be retained in position, as described above, using conventional removable adhesives. Alternatively, the plurality of electrodes 12 can be retained in position using the adjustable belt-like structure 23, as described above with respect to FIGS. 2A and 2B.

At step 115, an operator may define a depth "d" at which a nerve is to be blocked by estimating the distance from the skin (e.g. edge of nerve blocking plane 16a) to the sample nerve 18 to be blocked. In one embodiment, the depth "d" can range from approximately 1.5 centimeters (cm) to approximately 3 cm if the nerve blocking plane 16a is defined on a patent's thigh 14a region. The particular depth in any procedure will, of course, depend upon a variety of factors including but not limited to the location of the nerve.

At step 120, an operator may insert the first end 20a of the conductive needle 20 into the nerve blocking plane 16a to the depth "d", the periphery of which includes the plurality of electrodes 12 for forming the bounded area 16. At step 125, the pulse generator 22 and the multi-position switch 24 are controlled to sequentially permit at least one pulse to be communicated from the first end 20a (e.g., tip) of conductive needle 20 to each one of the plurality of electrodes 12 in a predetermined sequence, which will be described in further detail below in connection with FIG. 3.

At step 130, in the exemplary embodiment, an operator can visually observe one or more actual muscle contractions in the thigh region 14a in response to each pulse communicated from the first end 20a of the conductive needle 20. Although not specifically shown, each observed muscle contraction can be captured by a camera and an image thereof digitally stored in the database 30. At the operator's discretion, one or more of the captured and stored actual muscle contractions images can be played on the image display 28, so that the operator can study attributes of the actual muscle contraction without having to apply subsequent pulses from the first end 20a of the conductive needle to again stimulate the sample nerve 18.

At step 135, the operator can compare each of the actual muscle contractions in response to each of the sequential pulses or the captured and stored versions thereof with a model muscle contraction selected from a library of model muscle contractions to determine if a substantial match exists. The library of model muscle contractions is stored in the database 30. At step 140, if it is determined that attributes of each actual muscle contraction do not substantially match attributes of the model muscle contraction, the method 100 includes moving or relocating the first end 20a of the conductive needle 20 to another location in the nerve blocking plane 16a, which is bounded by the plurality of electrodes 12, and again inserting to first end 20a of the conductive needle 20 into the nerve blocking plane 16a to the depth "d." Thereafter, the method 100 is redirected back to step 125 for repeating the above described process until it is determined that attributes of at least one of the actual muscle contractions substantially match attributes of the model muscle contraction. If it is determined that attributes of at least one actual muscle contraction substantially match attributes of the model muscle contraction, the method 100 continues to step 150. In an embodiment, attributes of each actual muscle contraction used to substantially match attributes of the model muscle contraction can include the forcefulness of the muscle contraction, where the greatest forcefulness of a muscle contraction occurs when the sample nerve 18, which is innervating the muscle, lies between the first end 20a of the conductive needle 20 and one of the plurality of electrodes 12.

The model muscle contractions stored in the database 30 can include a plurality of digitally compressed and stored images of muscle contractions, which are expected to be received in response to excitation of a number of predetermined nerves. In the exemplary embodiment, the sample nerve 18 is defined as a popliteal nerve, which traverses the patient's thigh 14a region. Thus, for example, an operator would parse the database 30 to locate a model muscle contraction for a popliteal nerve and subsequently display the model muscle contraction on the image display 28. Further, the operator can compare an actual muscle contraction viewed in response to excitation of the popliteal nerve with the model muscle contraction of the popliteal nerve displayed on the image display 28.

At step 150, after it is determined that attributes (e.g., forcefulness) of at least one actual muscle contraction substantially match attributes of the model muscle contraction, the method 100 further includes determining a relative spatial relationship between the first end of the conductive needle 20 and one of the plurality of electrodes 12. More specifically, as each pulse is sequentially communicated from the first end 20a of the conductive needle 20 to each of the plurality of electrodes 12, the operator can study and compare a corresponding number of actual muscle contractions to the model muscle contraction displayed on the image display 28. When the sample nerve 18 is substantially located along a path defined between the first end 20a of the conductive needle 20 and one of the plurality of electrodes 18, the closest substantial match between the actual muscle contraction and the model muscle contraction will be obtained. For example, the closest substantial match between the actual muscle contraction, which results from excitation of the sample nerve 18, and the model muscle contraction associated with the sample nerve will be obtained when the first end 20a of the conductive needle 20 communicates a pulse to electrode "j," because the sample nerve 18 is substantially located along a path defined between the first end 20a of the conductive needle 20 and the electrode "j."

At step 155, a distance value representing the distance between the first end 20a of the conductive needle 20 and the sample nerve 18 can be determined. In an embodiment, the distance value is determined in accordance with Coulomb's law, $E=K(Q/r^2)$, where E=energy required to activate the nerve or current density (e.g., electrical current per unit of cross section area); K=a constant; Q=minimal current density required to trigger the muscle contraction by stimulating the sample nerve 18. If current remains constant and the sample nerve 18 is located between the electrode "j" and the first end 20a of the conductive needle 20, the closer the first end 20a of the conductive needle 20 is to the sample nerve 18, the larger the current density. Knowing the values of E, K, and Q, the distance (r) between the first end 20a of the conductive needle 20 and the sample nerve 18 can be determined.

At step 160, the processor can process the relative spatial relationship between first end 20a of the conductive needle 20 and the sample nerve 18 and the distance value representing the distance between the first end 20a of the conductive needle 20 and the sample nerve 18 to generate an image displaying a proximity of the first end 20a of the conductive needle 20 to the sample nerve 18. The image displaying the proximity of the first end 20a of the conductive needle 20 to the sample nerve 18 can be shown on the image display 28, so that the operator can move the first end 20a of the conductive needle 20, under interactive guidance of the image, to a nerve-blocking position with respect to the sample nerve 18. Thereafter, the operator can depress the injection button 20c located on the second end 20b of the conductive needle 20 to administer a nerve blocking agent or solution to the nerve-blocking position to locally anesthetize the sample nerve 18.

Figure 4:
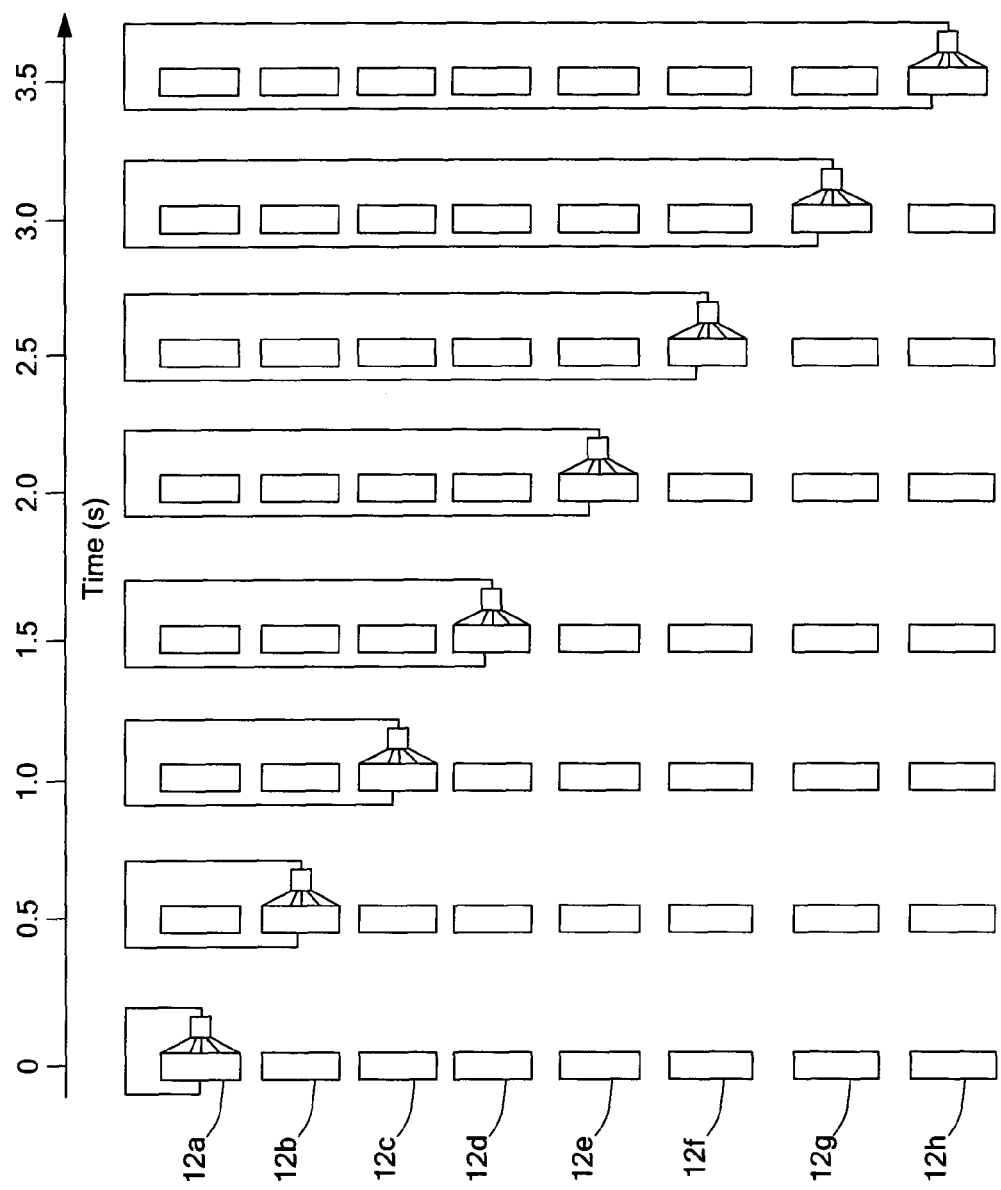
FIG. 4 is a schematic illustration of one embodiment of a sequence for which at least one electrical pulse is communicated between the first end of a conductive needle and each of a plurality of electrodes.

Referring now to FIG. 4, shown is a schematic illustration of one embodiment of a sequence for which at least one electrical pulse is communicated between the first end 20a (FIG. 1A) of the conductive needle 20 (FIG. 1A) and each one of the plurality of electrodes 12) (FIG. 1A). In the exemplary embodiment, a first pulse is communicated between the first end 20a of the conductive needle 20 and electrode "12a" at time equals 0 seconds. A second pulse is communicated between the first end 20a of the conductive needle 20 and electrode "12b" at time equals 0.5 seconds. A third pulse is communicated between the first end 20a of the conductive needle 20 and electrode "12c" at time equals 1 second. A fourth pulse is communicated between the first end 20a of the conductive needle 20 and electrode "12d" at time equals 1.5 seconds. A fifth pulse is communicated between the first end 20a of the conductive needle 20 and electrode "12e" at time equals 2 seconds. A sixth pulse is communicated between the first end 20a of the conductive needle 20 and electrode "12f" at time equals 2.5 seconds. A seventh pulse is communicated between the first end 20a of the conductive needle 20 and electrode "12g" at time equals 3 seconds. An eighth pulse is communicated between the first end 20a of the conductive needle 20 and electrode "12h" at time equals 3.5 seconds.

In the exemplary embodiment, the first through eighth pulses include constant current values of approximately 1.4 mA and have pulse widths of approximately 0.2 ms. It should be understood that a number of other sequences for which at least one electrical pulse is communicated between the first end 20a of the conductive needle 20 and one of the plurality of electrodes 12 can be employed with departing from principles of the present invention. It should be appreciated, however, that the pulse shapes, current values and durations can be varied depending upon a variety of factors, such as the location of the nerve blocking plane (e.g. plane 16a in FIG. 1) on the patient's body, the depth "d" for which the conductive needle 20 is inserted and the nature or characteristics of the sample nerve 18 to be excited. It should also be appreciated that even though the exemplary embodiment utilizes a sequence of pulses in clockwise order (e.g. beginning at electrode 12a) other sequences are also possible. For example, the sequence of electrodes could be in counter clockwise order (e.g. beginning at electrode 12h and ending with electrode 12a). Also, it may be desirable to utilize a sequence of which includes every other electrode. Alternatively still, any arbitrary sequence can also be used. Furthermore, in some embodiments and/or applications, it may not be necessary or desirable to provide a pulse to each electrode.

Having thus described at least one illustrative embodiment of the invention, various alterations, modifications and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto. All references and publications cited herein are expressly incorporated herein by reference in their entirety.

What is claimed is:

1. A system for providing nerve mapping, the system comprising:

a processor;

a pulse generator coupled to the processor;

a conductive needle having a first end adapted for insertion into tissue and a second end coupled to a first terminal of the pulse generator;

a switch having an input, a control input and a plurality of outputs, the input being coupled to a second terminal of the pulse generator and the control input being coupled to the processor; and a plurality of electrodes arranged into a ring defining a bounded area and each being coupled to a corresponding one of the plurality of outputs of the switch, wherein the control input is adapted to receive a plurality of control signals from the processor for selectively coupling the second terminal of the pulse generator to one of the plurality of electrodes, and wherein at least one pulse is applied to the first end of the needle while the conductive needle is positioned in the bounded area to form a communication relationship between the first end of the needle and at least one of the plurality of electrodes for exciting a nerve located in the bounded area.

2. The system of claim 1, further comprising a video image display coupled to the processor and being adapted to provide at least one image depicting a proximity of the first end of the needle and the nerve.

3. The system of claim 1, further comprising a non-conductive medium adapted to retain each of the plurality of electrodes in the ring and having a predetermined spacing relative to each other for defining the bounded area.

4. The system of claim 1 wherein the conductive needle comprises a control for adjusting an energy value of the at least one pulse to permit a minimal energy value to be applied to the first end of the needle to excite the nerve.

5. The system of claim 1 wherein the at least one pulse comprises a pulse width ranging from approximately 0.1 milli-seconds to approximately 0.5 milli-seconds.

6. The system of claim 5 wherein the at least one pulse comprises a current output ranging from approximately zero milli-amperes to approximately 2 milli-amperes.

7. The system of claim 1 wherein the switch comprises a solid-state switch.

8. The system of claim 1 wherein the switch comprises a multiplexor.

9. A method for providing nerve mapping, the method comprising:

(a) applying at least one pulse to a first end of a conductive needle while positioning the conductive needle at a predetermined position in a region of tissue bounded by a plurality of electrodes for forming a communication relationship between the first end of the conductive needle and at least one electrode of the plurality of electrodes to excite a predetermined nerve located in the region of the tissue bounded by the plurality of electrodes; and (b) measuring at least one actual muscle contraction between the first end of the needle and the at least one electrode of the plurality of electrodes in response to excitation of the predetermined nerve.

10. The method of claim 9 wherein prior to applying the at least one pulse, the method further comprises determining a proximate nerve blocking location on the region of tissue for which the predetermined nerve is to be blocked.

11. The method of claim 10 further comprising disposing the plurality of electrodes on the nerve blocking location in a ring arrangement to form the region of the tissue bounded by the plurality of electrodes.

12. The method of claim 11, further comprising defining a proximate depth "d" at which the predetermined nerve is to be blocked.

13. The method of claim 12 wherein positioning the conductive needle at the predetermined position located in the region of tissue bounded by the plurality of electrodes comprises inserting the first end of the conductive needle to the proximate depth "d."

14. The method of claim 9 wherein measuring the at least one actual muscle contraction comprises comparing the at least one actual muscle contraction to a model muscle contraction.

15. The method of claim 14, further comprising determining if the at least one actual muscle contraction substantially matches the model muscle contraction.

16. The method of claim 15 wherein if it is determined that the at least one actual muscle contraction substantially matches the model muscle contraction, the method further comprising determining a relative spatial relationship between the first end of the conductive needle and the predetermined nerve.

17. The method of claim 16, further comprising determining a distance value between the first end of the conductive needle and the predetermined nerve.

18. The method of claim 17, further comprising processing the relative spatial relationship and the distance value to generate a needle position image displaying a relative proximity of the first end of the conductive needle to the predetermined nerve.

19. The method of claim 18, further comprising moving the first end of the needle under interactive guidance of the needle position image to a nerve blocking position for administration of a nerve blocking agent.

20. The method of claim 15 wherein if it is determined that the at least one actual muscle contraction does not substantially match the model muscle contraction, the method further comprises moving the tip of the needle to another predetermined position in the region of tissue bounded by the plurality of electrodes and repeating steps (a) and (b).

21. The method of claim 14 wherein comparing the at least one actual muscle contraction to the model muscle contraction comprises comparing the at least one actual muscle contraction to a rendering of the model muscle contraction.

22. The method of claim 21 wherein comparing the at least one actual muscle contraction to the rendering of the model muscle contraction comprises comparing the at least one actual muscle contraction to the model muscle contraction rendered on a display.

23. A method for nerve mapping comprising:

a. arranging a plurality of electrodes to form a bounded region on a surface;

b. positioning a conductive needle within the bounded region;

c. providing a first conductive path between the conductive needle and a first one of the plurality of electrodes;

d. applying at least one electrical pulse to the bounded region through the conductive needle; and e. measuring a first nerve response through the first conductive path;

f. providing a second conductive path between the conductive needle and a second one of the plurality of electrodes;

g. applying an additional at least one electrical pulse to the bounded region through the conductive needle; and h. measuring a second nerve response through the second conductive path.

24. The method of claim 23 wherein measuring the first nerve response and measuring the second nerve response comprises comparing muscle contractions to model muscle contractions.

25. The method of claim 24 wherein comparing muscle contractions to model muscle contractions comprises comparing muscle contractions to renderings of the model muscle contractions.

* * * * *

UNITED STATES PATENT AND TRADEMARK OFFICE
CERTIFICATE OF CORRECTION

PATENT NO.        : 7,104,965 B1
APPLICATION NO. : 10/456823
DATED             : September 12, 2006
INVENTOR(S)       : Yandong Jiang et al.

It is certified that error appears in the above-identified patent and that said Letters Patent is hereby corrected as shown below:

Column 1, line 56, delete "patients skin" and replace with -- patient's skin --.

Column 2, line 34, delete "level of which the nerve to be blocked." and replace with -- level at which the nerve is to be blocked. --.

Column 3, line 4, delete "of the inventions," and replace with -- of the invention, --.

Column 4, line 6, delete "BRIEF DESCRIPTION OF THE DRAWING" and replace with -- BRIEF DESCRIPTION OF THE DRAWINGS --.

Column 4, lines 30-31, delete "in human body" and replace with -- in the human body--.

Column 4, lines 40-41, delete "in human body" and replace with -- in the human body --.

Column 4, line 46, delete "are couples" and replace with -- are coupled --.

Column 5, line 45, delete "patent's right" and replace with -- patient's right --.

Column 5, line 64, delete "patent's right" and replace with -- patient's right --.

Column 6, line 2, delete "patent's right" and replace with -- patient's right --.

Column 6, lines 6-7, delete "electrodes secured the patients" and replace with -- electrodes that secured the patient's --.

Column 6, line 9, delete "patients" and replace with -- patient's --.

Column 6, line 10, delete "patients" and replace with -- patient's --.

Column 6, line 11, delete "patients" and replace with -- patient's --.

Column 6, line 56, delete "is provide" and replace with -- is provided --.

Column 7, line 7, "couple in series" and replace with --coupled in series --.

Column 7, line 56, "patent's" and replace with -- patient's --.

Column 7, line 62, "patent's" and replace with -- patient's --.

Column 8, line 13, "patent's" and replace with -- patient's --.

UNITED STATES PATENT AND TRADEMARK OFFICE
CERTIFICATE OF CORRECTION

PATENT NO. : 7,104,965 B1
APPLICATION NO. : 10/456823
DATED : September 12, 2006
INVENTOR(S) : Yandong Jiang et al.

It is certified that error appears in the above-identified patent and that said Letters Patent is hereby corrected as shown below:

Column 8, line 34, "muscle contractions images" and replace with -- muscle contraction images --.

Column 10, line 10, "electrodes 12)" and replace with -- electrodes 12--.

Signed and Sealed this

Third Day of April, 2007

JON W. DUDAS
*Director of the United States Patent and Trademark Office*